United States Patent [19]

Cain

[11] Patent Number: 4,665,097
[45] Date of Patent: * May 12, 1987

[54] NOVEL BICYCLOOXYARYL THIOUREAS AND PROCESS FOR PREPARATION

[75] Inventor: Paul A. Cain, Cary, N.C.

[73] Assignee: Union Carbide Corporation, Danbury, Conn.

[*] Notice: The portion of the term of this patent subsequent to Jan. 17, 2001 has been disclaimed.

[21] Appl. No.: 480,697

[22] Filed: Mar. 31, 1983

[51] Int. Cl.$^4$ ............... C07C 127/22; C07C 121/60; A01N 37/18; A01N 37/34
[52] U.S. Cl. ..................... 514/584; 544/160; 544/376; 546/269; 546/297; 549/15; 549/32; 549/51; 549/289; 549/399; 549/400; 549/401; 549/437; 549/467; 564/23; 558/413; 558/415; 560/163; 560/164; 260/456 A
[58] Field of Search .............. 260/453 RW, 465 D; 564/23; 424/298, 322; 514/584, 522; 558/413, 415

[56] References Cited

U.S. PATENT DOCUMENTS

| | | | |
|---|---|---|---|
| 3,748,356 | 7/1973 | Wellinga et al. | 260/465 E |
| 3,803,227 | 4/1974 | Joos et al. | 564/23 |
| 4,160,037 | 7/1979 | Kaugars | 564/23 X |
| 4,264,605 | 4/1981 | Suhr et al. | 424/263 |
| 4,275,077 | 1/1981 | Becher et al. | 424/322 |
| 4,276,310 | 1/1981 | Sirrenberg et al. | 514/584 |
| 4,310,530 | 1/1982 | Nishiyama et al. | 424/263 |
| 4,350,706 | 9/1982 | Brouwer et al. | 564/23 X |
| 4,426,385 | 1/1984 | Cain | 564/44 X |
| 4,457,943 | 7/1984 | Becher et al. | 564/23 X |
| 4,468,405 | 8/1984 | Rigterink et al. | 564/23 X |
| 4,533,676 | 8/1985 | Sirrenberg et al. | 514/584 X |

FOREIGN PATENT DOCUMENTS 0017484  10/1980  European Pat. Off. .

*Primary Examiner*—Joseph Paul Brust
*Attorney, Agent, or Firm*—Gerald L. Coon

[57] ABSTRACT

Novel bicyclooxyaryl thioureas are provided together with methods for their preparation and use as the active toxicant in pesticidal compositions.

30 Claims, No Drawings

NOVEL BICYCLOOXYARYL THIOUREAS AND PROCESS FOR PREPARATION

FIELD OF INVENTION

This invention relates in general to novel bicyclooxyaryl thioureas which are useful as the active toxicant in pesticidal compositions. In one aspect, this invention relates to a method for the preparation of the novel thioureas. In a further aspect this invention is directed to pesticidal compositions and to a method for their use.

BACKGROUND OF THE INVENTION

In recent years a variety of polycyclic urea compounds have been reported in the literature as having pesticidal activity. For example, U.S. Pat. No. 3,992,553 which issued on Nov. 16, 1976, U.S. Pat. No. 4,041,177 which issued on Aug. 9, 1977, and U.S. Pat. No. 4,275,077 which issued June 23, 1981 all disclose certain benzoyl-ureas which were indicated to possess insecticidal properties. 1-Benzoyl-3-(substituted phenyl) thioureas have been described in U.S. Pat. Nos. 3,748,356; 3,933,908, 3,989,842; 4,234,600; 4,276,310 and 4,160,037. In these patents the phenyl ring has usually been substituted with halogen, alkyl, alkoxy, haloalkyl, haloalkoxy and the like. Benzoyl thioureas of substituted pyridyl amines and of isoxazolyl amines have been disclosed in U.S. Pat. No. 4,264,605 and U.S. Pat. No. 4,336,264 respectively. Insecticidal 1-benzoyl-3-pyridyloxyphenyl thioureas and 1-benzoyl-3-pyridyloxyphenyl thioureas have been disclosed in U.S. Pat. No. 4,310,530 and J. Kokai 81 15,272 respectively. 1-Benzoyl-3-(4-[trifluoromethylsulfonylphenoxy]phenyl)thioureas are disclosed in J. Kokai 81 25, 148 to as insecticides.

Accordingly, one or more of the following ojects will be achieved by the practice of this invention. It is an object of this invention to provide certain novel bicyclooxyaryl thioureas. Another object of this invention is to provide novel bicyclooxyaryl thioureas which exhibit excellent insecticidal activity. A still further object of this invention is to provide novel compounds such as 1-(4-4-[chloro-1-naphthoxy]-3,5-dichlorophenyl)-3-(2,6-difluorobenzoyl)thiourea and the like. Another object is to provide processes for the preparation of the novel thioureas. A further object is to provide novel pesticidal compositions containing the novel thioureas as the active toxicant. Another object of this invention is to provide a method for controlling pests by the application of the novel pesticidal compositions. These and other objects will readily become apparent to those skilled in the art in the light of the teachings herein set forth.

SUMMARY OF THE INVENTION

In its broad aspect the invention relates to novel bicyclooxyaryl thioureas, pesticidal compositions containing the same, and processes for their preparation and use. The thioureas of this invention can be represented by the following formula (I):

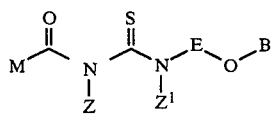    I wherein M, Z, Z', E and B are as hereinafter indicated.

DETAILED DESCRIPTION OF THE INVENTION

As indicated above, the novel bicyclooxyaryl thioureas of this invention are conveniently represented by the formula:

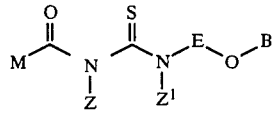    I wherein:

M represents a monocyclic aromatic ring system or a monocyclic heterocyclic ring system containing up to two nitrogen atoms and M can contain up to four X substituents, each of which individually can be halogen, nitro, cyano or alkyl, polyhaloalkyl alkoxy, or polyhaloalkoxy of from one to three carbon atoms;

Z and $Z^1$ individually are hydrogen, $C_{1-6}$ alkyl or $C_{1-6}$ alkyl which may be substituted by at least one halogen, hydroxy or alkoxy;

E is a six membered carbocyclic aromatic ring or a five or six membered heterocyclic ring containing up to two oxygen, sulfur or nitrogen atoms or a combination thereof, and wherein thus ring may contain up to four Y substituents wherein each Y individually can be halogen, cyano or alkyl, polyhaloalkyl, alkoxy, polyhaloalkyoxy, alkylsulfenyl, or polyhaloalkylsulfenyl of from one to six carbon atoms;

B is a bicyclic fused ring system which is attached to the oxygen through a carbocyclic ring and wherein (a) at least one ring is six-membered, unsaturated and carbocyclic and which contains the substituents $R^1$ and $R^2$ (b) the second ring, hereinafter also referred to as A, when it is not a five or six-membered saturated or unsaturated carbocyclic can be a five or six-membered saturated or unsaturated heterocyclic which can contain in any combination a carbonyl group or one or two oxygen or sulfur atoms and the substituents $R^3$ and $R^4$ attached to unsaturated ring carbons or the substituents $R^5$ and $R^6$ attached to saturated ring carbons;

$R^1$ and $R^2$ individually may be hydrogen, halogen, nitro, cyano, amino, formamido, formamidino, phenylsulfenyl, phenylsulfinyl, phenylsulfonyl, phenylsulfamido, or phenoxysulfonyl, wherein the phenyl ring optionally may contain one or more substituents, selected from halogen, nitro, or alkyl, polyhaloalkyl, alkoxy, or polyhaloalkoxy of from one to three carbon atoms, or $R^1$ and $R^2$ individually may be alkyl, alkoxy, polyhaloalkyl, polyhaloalkoxy, alkenyloxy, polyhaloalkenyloxy, alkynyloxy, polyhaloalkynyloxy, alkylsulfenyl, alkylsulfonyl, polyhaloalkylsulfenyl, alkylsulfinyl, mono- or di-alkylsulfamido, mono-or di-alkylamino, alkylcarbonylamino, alkoxycarbonylamino, mono-or di-alkylamino carbonyloxy, alkoxysulfonyl, polyhaloalkyloxysulfonyl of up to six carbons in each alkyl chain, morphilinosulfonyl or the group $SO_3Na$;

$R^3$ and $R^4$ can individually be hydrogen, halogen, nitro, cyano, or alkyl, polyhaloalkyl, alkoxy, polyhaloalkoxy, alkylsulfinyl, alkylsulfenyl, alkylsulfonyl, alkoxycarbonylamino or alkylcarbonylamino of from one to eight carbons, and $R^5$ and $R^6$ individually can be hydrogen, alkyl or polyhaloalkyl from one to six carbon atoms or phenyl which may be optionally substituted with up to three halogen, cyano, nitro or alkyl, polyhaloalkyl, alkoxy or polyhaloalkoxy of up to three carbon atoms.

Thus in formula (I) above, the B groups may be represented by the moiety

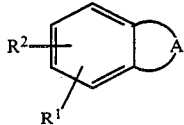

wherein $R^1$, $R^2$ and A are as defined above, and wherein the linking oxygen is attached to the unsaturated carbocyclic ring.

Illustrative but not inclusive of those aryl ether compounds wherein the B group with the oxygen attachment to the remainder of the molecule is one of the following:

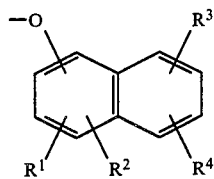

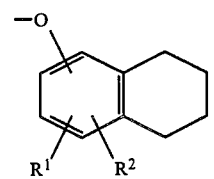

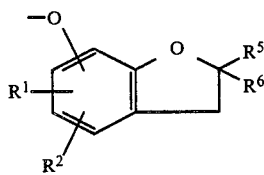

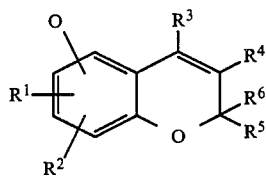

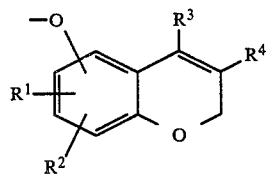

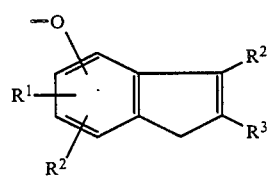

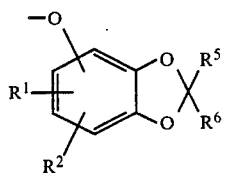

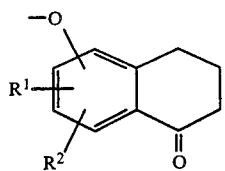

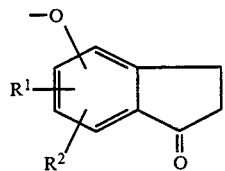

wherein $R^1$–$R^6$ are as previously indicated.

Another preferred class of compounds coming within the above generic formula can be represented by:

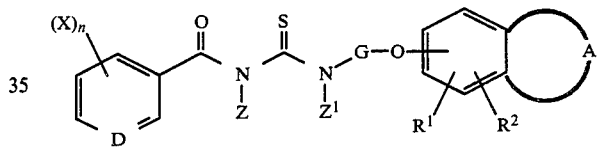

wherein: D is nitrogen or carbon radical, G is a phenyl ring or a six-membered heterocyclic ring containing one or two nitrogen atoms. G may contain up to four Y substituents. X, Y, Z, $Z^1$, $R^1$, $R^2$ and A are as previously indicated while n has a value of zero to four.

Particularly preferred compounds of this invention are those in which the G moiety is a phenyl or pyridine ring. Thus these compounds can be conveniently represented by the following formula:

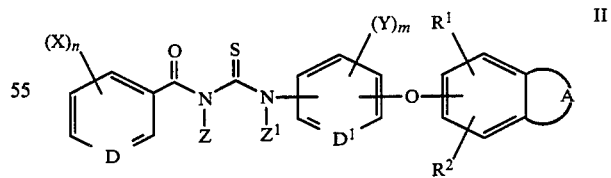

wherein: M is zero to four, $D^1$ is a carbon radical or nitrogen and the other substituents are as previously indicated. This invention also encompasses and N-oxide and addition salt complexes of the pyridine moieties.

Also particularly preferred compounds are those of the following formula in which Z and $Z^1$ are hydrogen, D and $D^1$ are carbon radicals:

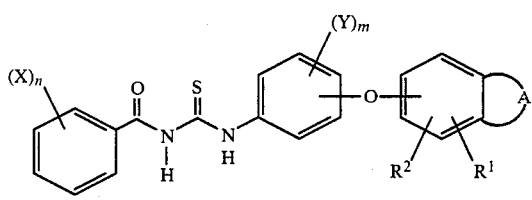

III

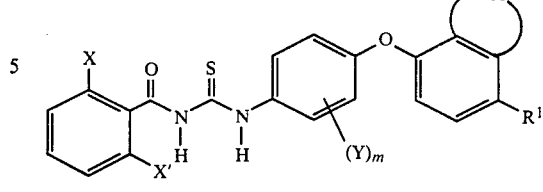

IV wherein: X, Y, $R^1$ and $R^2$, A, m and n are as previously described.

The most preferred compounds are those represented by the following formula:

wherein X, $X^1$, Y and m are as previously indicated and A is a tetramethylene group ($-CH_2)_4-$, or a 1,3-butadienylene group, $-CH=CH-CH=CH-$.

It is readily apparent that the preceding formula encompass a wide variety of novel compounds. Illustrative compounds of the invention are set forth in Tables 1–8 below:

TABLE 1
1-(4-[1-Naphthoxy]phenyl)-3-benzoyl Thioureas

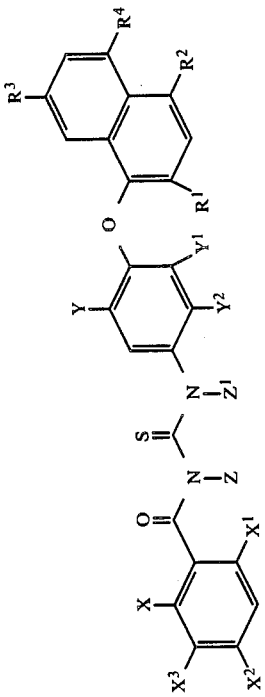

| X | X¹ | X² | X³ | Y | Y¹ | Y² | Z | Z¹ | R¹ | R² | R³ | R⁴ |
|---|----|----|----|----|----|----|----|----|----|----|----|----|
| F | F | H | H | Cl | Cl | H | H | H | H | N(CH₃)₂ | H | H |
| Cl | H | H | H | Cl | Cl | H | H | H | H | N(CH₃)₂ | H | H |
| F | F | H | H | CH₃ | Cl | CH₃ | H | H | H | N(CH₃)₂ | H | H |
| Cl | F | H | H | CH₃ | Cl | CH₃ | CH₃ | CH₃ | H | N(CH₃)₂ | H | H |
| Cl | H | H | H | CH₃ | H | CH₃ | H | CH₃ | H | N(CH₃)₂ | H | H |
| Cl | F | H | H | CH₃ | CH₃ | H | H | H | H | OCH₃ | H | H |
| F | F | H | H | CH₃ | CH₃ | H | H | H | H | OCH₃ | H | H |
| Cl | H | H | H | CH₃ | CH₃ | CH₃ | H | CH₃ | H | OCH₃ | H | H |
| Cl | F | H | H | CH₃ | Cl | CH₃ | H | CH₃ | H | OCH₃ | H | H |
| F | F | H | H | Cl | H | H | H | H | H | OCH₃ | H | H |
| Cl | F | H | H | Cl | CH₃ | H | H | CH₃ | H | NO₂ | H | H |
| F | F | H | H | Cl | H | H | H | H | H | NO₂ | H | H |
| CH₃ | OCH₃ | H | H | CH₃ | H | H | H | H | H | CN | H | H |
| OCH₃ | F | H | H | CH₃ | H | H | H | H | H | CN | H | H |
| F | F | H | H | CH₃ | CH₃ | CH₃ | H | H | Cl | Cl | H | H |
| NO₂ | Cl | H | H | CH₃ | Cl | H | H | H | Cl | Cl | H | H |
| Cl | H | Cl | H | Cl | Cl | H | H | H | H | N(n-C₄H₉)₂ | H | H |
| Cl | Cl | H | H | H | H | H | H | H | H | O=NCCH₃ H | H | H |
| F | F | H | H | H | H | H | H | H | H | O=NCCH(CH₃)₂ H | H | H |
| F | F | H | H | CH₃ | CH₃ | CH₃ | H | H | H | O=NCOC₂H₅ | H | H |
| F | H | Cl | Cl | CH₃ | Cl | CH₃ | H | H | H | O=OCN(CH₃)₂ | H | H |
| H | H | H | H | CH₃ | H | CH₃ | H | H | H | O=OCN(CH₃)₂ | H | H |

TABLE 1-continued 1-(4-[1-Naphthoxy]phenyl)-3-benzoyl Thioureas

| X | X¹ | X² | X³ | Y | Y¹ | Y² | Z | Z¹ | R¹ | R² | R³ | R⁴ |
|---|---|---|---|---|---|---|---|---|---|---|---|---|
| H | CH₃ | Cl | H | Cl | CH₃ | CH₃ | H | H | H | O—n-C₆H₁₃ | H | H |
| CH₃ | CH₃ | H | H | CH₃ | CH₃ | CH₃ | H | H | H | O—CH₂CH=CH₂ | H | H |
| CF₃ | CF₃ | H | Cl | CN | H | CH₃ | —n-C₆H₁₃ | H | H | OCH₂CH=CCl₂ | CH₃ | Cl |
| OCH₃ | OCH₃ | Cl | H | i-C₃H₇ | CH₃ | OCH₃ | H | i-C₃H₇ | H | Cl | OCH₃ | H |
| O—n-C₅H₁₁ | H | H | H | CH₃ | CH₃ | H | H | —(CH₂)₄OH | H | H | H | CF₃ |
| H | H | OCF₂H | NO₂ | CF₃ | CH₃ | OCH₃ | CH₃ | —CH₂CF₃ | Cl | OCH₃ | H | OCH₃ |
| H | CN | H | H | H | H | H | —CH₂OCH₃ | OCH₃ | Br | H | H | OCH₃ |
| F | CN | H | H | NO₂ | S—i-C₄H₉ | CH₃ | CH₃ | CH₃ | H | Br | H | OCH₂CH=CH₂ |
| Br | Br | H | H | H | H | CH₃ | CH₃ | CH₃ | H | CH₃ | H | OCH₃ |
| F | F | F | H | OCF₃ | H | CN | —n-C₄H₉ | H | CH₃ | Cl | H | OCF₃ |
| F | H | H | H | Cl | Cl | H | H | H | H | SO₂N(CH₃)₂ | H | H |
| Cl | H | H | H | CH₃ | Cl | CH₃ | H | H | Cl | H | H | H |
| H | H | OC₆H₁₂ | H | SCF₃ | Cl | CH₃ | H | H | Br | SO₂N—n-C₄H₉ | H | H |
| Cl | Cl | H | H | H | Cl | CH₃ | H | H | NO₂ | H | H | H |
| F | F | H | H | OC₆H₁₃ | CH₃ | H | (CH₂)₄OCH₃ | H | H | SO₂NC₆H₆ | H | H |
| H | H | H | H | H | Cl | n-C₄H₉ | (CH₂)₃CF₃ | H | H | H | H | H |
| H | CN | H | H | H | CH₃ | SCH₃ | H | H | H | SO₃C₆H₆ | H | H |
| H | CN | H | H | H | H | H | H | n-C₄H₉ | H | SO₃-(4-Cl-C₆H₄) | H | H |
| | | | | | | | | | | SO₃-(2,4-di-CH₃-C₆H₃) | | |
| NO₂ | H | H | H | H | H | H | H | H | H | S-(4-NO₂-C₆H₄) | O=NCOCH₃ | H |

TABLE 1-continued 1-(4-[1-Naphthoxy]phenyl)-3-benzoyl Thioureas

| X | X¹ | X² | X³ | Y | Y¹ | Y² | Z | Z¹ | R¹ | R² | R³ | R⁴ |
|---|---|---|---|---|---|---|---|---|---|---|---|---|
| OCF₂H | H | Cl | H | Cl | Br | H | (CH₂)₆OH | H | H | S-(2-CH,4-Cl-C₆H₃) | Cl | NCOC₆H₁₃ (O=), H |
| H | H | Cl | Cl | CN | CN | S—C₃H₇ | H | (CH₂)₄CCl₃ | SO₂CF₃ | SO₂CF₃ | SO₂CF₃ | Cl |
| F | F | F | H | OCH₃ | OCH₃ | SCF₃ | CH₃ | n-C₃H₇ | H | H | NO₂ | SO₂C₄H₉ |
| H | H | NO₂ | Cl | CF₃ | CH₃ | H | CH₃ | CH₃ | H | H | O=SC₂H₅ | CN |
| OC₃H₇ | OC₃H₇ | H | H | OCH₃ | H | OCH₃ | CH₃ | i-C₄H₉ | H | H | H | O=SC₃H₇ |
| F | F | OC₂H₅ | H | OC₃H₇ | Cl | H | SC₄H₉ | H | H | H | O=OCNC₄H₉, H | H |
| H | H | H | H | OCF₂CF₃ | H | CN | i-C₃H₇ | n-C₆H₁₃ | H | H | H | O=OCN(CH₃)₂ |
| F | F | H | H | CH₃ | CH₃ · Cl | CH₃ | H | H | S(=O)₂-morpholinyl | H | H | H |
| Cl | F | H | H | CH₃ | H | Cl | H | H | SO₃Na | H | H | H |

TABLE 2

1-(4-[5,6,7,8-Tetrahydro-1-naphthoxy]phenyl)-3-benzoyl Thioureas

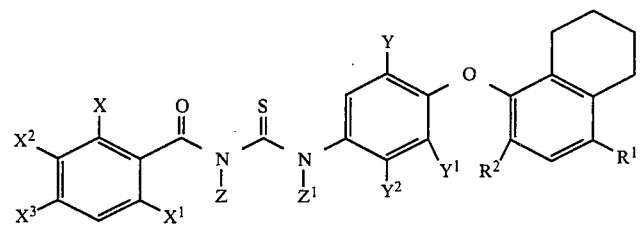

| X | $X^1$ | $X^2$ | $X^3$ | Y | $Y^1$ | $Y^2$ | Z | $Z^1$ | $R^1$ | $R^2$ |
|---|---|---|---|---|---|---|---|---|---|---|
| Cl | H | H | H | Cl | Cl | H | H | H | $N(CH_3)_2$ | H |
| F | F | H | H | Cl | Cl | H | H | H | $N(CH_3)_2$ | H |
| Cl | H | H | H | $CH_3$ | Cl | $CH_3$ | H | H | $N(CH_3)_2$ | H |
| F | F | H | H | $CH_3$ | Cl | $CH_3$ | H | H | $N(CH_3)_2$ | H |
| F | F | H | H | Cl | H | $CH_3$ | H | H | $N(CH_3)_2$ | H |
| F | F | H | H | $CH_3$ | H | $CH_3$ | H | H | $N(CH_3)_2$ | H |
| Cl | F | H | H | Cl | Cl | H | H | H | Cl | Cl |
| Cl | H | H | H | $CH_3$ | Cl | H | H | H | Cl | Cl |
| F | F | H | H | $CH_3$ | H | $CH_3$ | H | H | Cl | $NO_2$ |
| F | F | H | H | $CH_3$ | Cl | $CH_3$ | H | H | Br | Br |
| F | F | H | F | $CH(CH_3)_2$ | $CH(CH_3)_2$ | H | $CH(CH_3)_2$ | $CH(CH_3)_2$ | $NO_2$ | $N(CH_3)_2$ |
| H | $SCH_3$ | $NO_2$ | H | $C_3F_7$ | H | H | $CH_3$ | H | H | H |
| $SC_6H_{13}$ | H | Cl | Cl | $CH_3$ | $CH_3$ | $CH_3$ | $OCH_3$ | H | H | $S-n-C_4H_9$ |
| Cl | H | $SCF_3$ | H | $n-C_6H_{13}$ | H | $n-C_6H_{13}$ | H | $(CH_2)_6OH$ | $SCH_3$ | $SCH_3$ |
| H | O—n-Bu | H | O—n-Bu | H | Cl | $i-C_4H_9$ | $(CH_2)_6OH$ | H | $S(CH_2)_3CH(CH_3)_2$ | Cl |

TABLE 3

1-(4-[2-Naphthoxy]phenyl)-3-benzoyl Thioureas

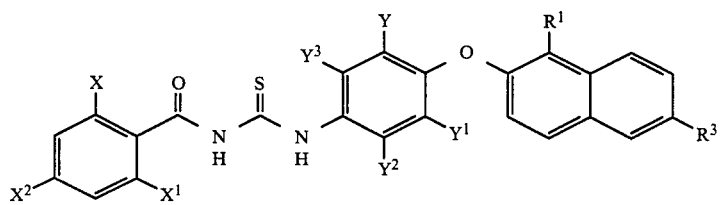

| X | $X^1$ | $X^2$ | Y | $Y^1$ | $Y^2$ | $Y^3$ | $R^1$ | $R^3$ |
|---|---|---|---|---|---|---|---|---|
| F | F | H | H | Cl | H | $CH_3$ | Br | Br |
| Cl | H | H | Cl | Cl | H | H | Br | Br |
| Cl | H | H | $CH_3$ | Cl | $CH_3$ | H | Br | Br |
| F | F | H | $CH_3$ | Cl | $CH_3$ | H | H | Br |
| H | $SCH(CH_3)_2$ | $SCH(CH_3)_2$ | $CH_3$ | $CH_3$ | $CH_3$ | H | $NO_2$ | Br |
| Cl | Cl | Cl | $CH_3$ | $CH_3$ | $CH_3$ | $CH_3$ | $CH_3$ | Cl |
| $CH_3$ | $CH_3$ | $CH_3$ | H | H | H | H | $NO_2$ | $NO_2$ |
| H | $OCH_3$ | $OCF_2H$ | H | H | $CH_3$ | $CH_3$ | $N(CH_3)_2$ | Br |
| $CH_3$ | Br | H | Cl | Cl | H | CN | $(CH_2)_4CH(CH_3)_2$ | H |
| H | H | $SCF_2Cl$ | H | H | $CF_3$ | H | $n-C_4H_9$ | Cl |
| H | H | $SCl_3$ | $C_2H_5$ | $n-C_6H_{13}$ | H | H | H | $OC_3H_7$ |
| H | H | CN | H | $CH_3$ | H | $SCH_3$ | $-CF_2(CH_2)_3CH_3$ | $NO_2$ |
| CN | H | H | H | $C_2H_5$ | H | $S-n-C_6H_{13}$ | $CF_2CF_3$ | Br |
| C | H | $NO_2$ | H | $OC_2H_5$ | H | $SCF_3$ | $NO_2$ | $\underset{\underset{O}{\parallel}}{\overset{\overset{O}{\parallel}}{S}}C_6H_{13}$ |
| F | $SC_3F_7$ | H | H | H | H | $SCF_2Cl$ | $SCH_3$ | $\underset{\underset{O}{\parallel}}{\overset{\overset{O}{\parallel}}{S}}CH_3$ |
| O—i-Bu | H | Cl | H | H | H | $SCF_2(CH_2)_3CH_3$ | CN | $SO_2N(CH_3)_2$ |

TABLE 4
1-(Bicyclooxyaryl)-3-benzoyl Thioureas

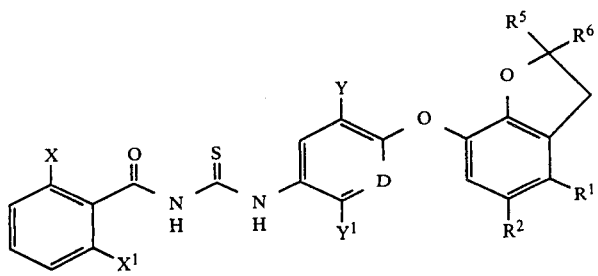

| X | X¹ | D | Y | Y¹ | R¹ | R² | R⁵ | R⁶ |
|---|---|---|---|---|---|---|---|---|
| F | F | CCl | Cl | H | Cl | H | $CH_3$ | $CH_3$ |
| Cl | H | CCl | $CH_3$ | $CH_3$ | $N(CH_3)_2$ | H | $CH_3$ | $CH_3$ |
| H | H | $CCH_3$ | $CH_3$ | H | Cl | H | $CH_3$ | $CH_3$ |
| F | F | $CCH_3$ | H | H | $N(CH_3)_2$ | H | $CH_3$ | $CH_3$ |
| F | F | $CH_3$ | $CH_3$ | $CH_3$ | $N(CH_3)_2$ | H | $CH_3$ | $CH_3$ |
| Cl | F | $CH_3$ | Cl | $CH_3$ | $N(CH_3)_2$ | H | $CH_3$ | $CH_3$ |
| Cl | H | $CH_3$ | $CH_3$ | $CH_3$ | Cl | H | $CH_3$ | $CH_3$ |
| H | H | $CH_3$ | Cl | $CH_3$ | Cl | H | $CH_3$ | $CH_3$ |
| F | F | CCl | $CH_3$ | $CH_3$ | Cl | H | $CH_3$ | $CH_3$ |
| Cl | H | CCl | $CH_3$ | $CH_3$ | Cl | H | $CH_3$ | $CH_3$ |
| H | H | CCl | Cl | H | Cl | H | $CH_3$ | $CH_3$ |
| H | Cl | CCl | Cl | H | Cl | H | $CH_3$ | $CH_3$ |
| Cl | H | CCl | Cl | H | Cl | Cl | $CH_3$ | $CH_3$ |
| F | F | CCl | $CH_3$ | $CH_3$ | Cl | Cl | $CH_3$ | $CH_3$ |
| F | Cl | $CH_3$ | Cl | $CH_3$ | Cl | Cl | $CH_3$ | $CH_3$ |
| F | Cl | $CH_3$ | Cl | $CH_3$ | Cl | Cl | $CH_3$ | $CH_3$ |
|  |  | N | Cl | H | Cl | H | $CH_3$ | $CH_3$ |
| $NC_2$ | CN | N | Cl | H | H | H | $CH_3$ | $CH_3$ |
| F | F | N | $CH_3$ | H | Cl | H | $CH_3$ | $CH_3$ |
| Br | Br | N | $CH_3$ | H | H | H | $CH_3$ | $CH_3$ |
| Cl | Br | N | Cl | Cl | Cl | H | $CH_3$ | $CH_3$ |
| Br | H | N | Cl | $CH_3$ | H | H | $CH_3$ | $CH_3$ |
| O $C_2H_5$ | H | N | H | Cl | Cl | H | $CH_3$ | $CH_3$ |
| F | $SCH(CH_3)_2$ | N | H | CH | H | H | $CH_3$ | $CH_3$ |
| Cl | $SCH_3$ | N | $SCCl_3$ | H | Cl | Cl | $CF_3$ | $CF_3$ |
| O—i-Bu | O—i-Bu | N | $CH_3$ | $(CH_2)_2CH(CH_3)_2$ | $NO_2$ | H | $CH_3$ | $n$-$C_6H_{13}$ |
| $SCH_3$ | $SCH_3$ | $CNO_2$ | $CH_3$ | Cl | H | CN | 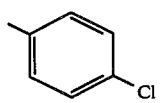 | H |
| $NO_2$ | Cl | N | Br | Br | H | H | $CF_3$ | $C_3F_7$ |
| Cl | H | N | F | F | H | H | $CH_3$ | 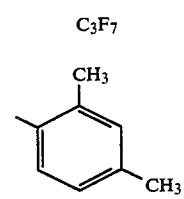 |
| F | F | N | $n$-$C_6H_{13}$ | $CHBrCH_2Br$ | H | H | 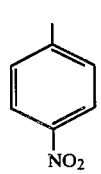 | H |
| H | H | CCN | CN | $CH_3$ | H | H | 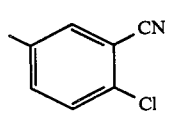 | $CF_3$ |

TABLE 5

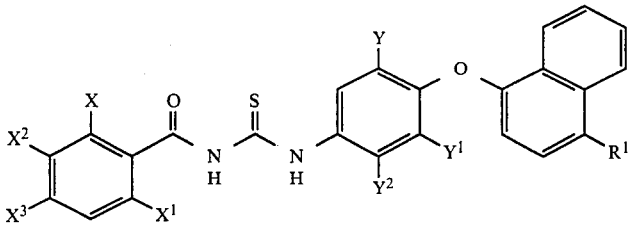

| X | X¹ | X² | X² | Y | Y¹ | Y² | R¹ |
|---|---|---|---|---|---|---|---|
| H | Cl | NO$_2$ | H | H | CH$_3$ | CH$_3$ | —N(H)CHO |
| H | H | H | NO$_2$ | CH$_3$ | H | SC$_6$H$_{13}$ | —N=CHN(CH$_3$)$_2$ |
| CN | F | H | H | CH$_3$ | H | SCH$_2$CHBrCCl$_3$ | —N(H)C(O)N(CH$_3$)$_2$ |
| H | CN | H | Cl | Cl | Cl | H | —O—CH$_2$C≡CH |
| H | Cl | H | CN | Cl | H | CH$_3$ | —O—CF$_2$C≡CH |
| SCH | H | H | SCH$_3$ | CH$_3$ | H | CH$_3$ | O—CH$_2$C≡CCl |
| SC$_2$H$_5$ | F | H | H | CH(CH$_3$)CH(CH$_3$)$_2$CH$_3$ | H | H | —SO$_2$CF$_3$ |
| H | H | Cl | Cl | H | H | H |  |
| H | CH$_3$ | CH$_3$ | H | Cl | CH$_3$ | H | SO$_2$-(3,4-dimethylphenyl) |
| CH(CH$_3$)$_2$ | F | H | H | Cl | OC$_3$Hg | H | S(O)-(2,4-dichlorophenyl) |
| H | H | H | C(CH$_3$)$_3$ | CH$_3$ | H | CN | S(O)CF$_3$ |
| CH(CH$_3$)$_2$ | C(CH$_3$)$_2$ | H | H | CH$_3$ | OCH(CN)CHCl$_2$ | H |  |
| Cl | Cl | H | Cl | CH$_3$ | CH$_3$ | CH$_3$ | SO$_2$CH$_2$C(Cl)=CH$_2$ |
| CH$_3$ | CH$_3$ | H | CH$_3$ | C$_2$H$_5$ | C$_2$H$_5$ | H | S(O)CH$_3$ |
| H | H | H | H | C$_6$H$_{13}$ | H | H | S(O)C$_6$H$_{13}$ |
| H | H | H | H | Cl | Cl | CH$_3$ | SO$_2$CH$_2$CH(CH$_3$)$_2$ |
| Cl | Cl | H | H | H | H | H | SO$_2$N(H)C$_2$H$_5$ |

TABLE 6

| D | D¹ | X | R³ | R⁴ | R⁵ | R⁶ |
|---|---|---|---|---|---|---|
| N | CH₃ | Cl | CH₂CH(CH₃)₂ | OC₂H₅ | CH₃ | CH₃ |
| N | CH₃ | F | CH₃ | C₆H₁₃ | CH₃ | CH₃ |
| CH₃ | N | CH₃ | OCH₃ | OCH₃ | CH₃ | CH₃ |
| N | N | OCH₃ | H | OC₅H₁₁ | CH₃ | CH₃ |
| N | N | OCF₃ | CH₂CHBrCCl₃ | H | CH₃ | CH₃ |
| N | N | OC₄H₉ | CH₃ | CCl₃ | CH₃ | CH₃ |
| CH₃ | CF | F | OCHCHCl₂ (with Cl) | H | CH₃ | CH₃ |
| CH₃ | CCl | H | H | H | 3,5-dichlorophenyl | CF₃ |
| CH₃ | CF | Cl | H | H | 4-nitrophenyl | H |
| CH₃ | CH | Cl | H | H | C₃H₇ | 4-chloro-2-nitrophenyl |
| CNO₂ | CH | Cl | H | H | 4-(OCF₃)phenyl | H |

TABLE 7

| X | X¹ | Y | Y¹ | Y² | R⁵ | R⁶ |
|---|---|---|---|---|---|---|
| F | F | Cl | Cl | H | CH₃ | CH₃ |
| Cl | H | CH₃ | Cl | CH₃ | CH₃ | CH₃ |
| F | F | CH₃ | Cl | CH₃ | CH₃ | CH₃ |
| Cl | F | Cl | H | CH₃ | CH₃ | CH₃ |
| H | Br | Cl | Cl | CH₃ | 3,4-dichlorophenyl | 4-chlorophenyl |
| Br | Br | CH₃ | H | CH₃ | n-C₆H₁₃ | n-C₄H₉ |
| F | Br | Cl | H | CH₃ | (CH₂)₄CHBrCH₂Br | CH₃ |
| CH₃ | CH₃ | CH₃ | CH₃ | CH₃ | CF₃ | CF₃ |

TABLE 7-continued

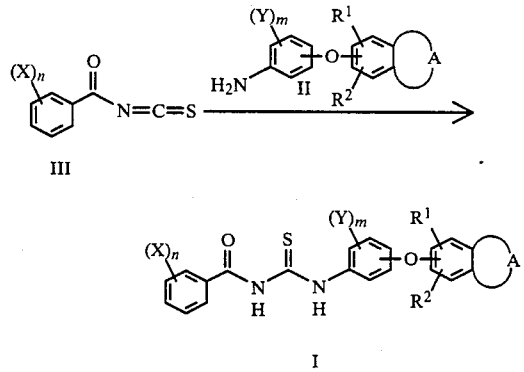

| X | X¹ | Y | Y¹ | Y² | R⁵ | R⁶ |
|---|---|---|---|---|---|---|
| OCH₃ | OCH₃ | Cl | Cl | H | CH₃ | CF₃ |

TABLE 8

| X | X¹ | R¹ | A |
|---|---|---|---|
| F | H | H | —(CH₂)₃C(=O)— |
| F | H | Cl | —(CH₂)₂C(CH₃)₂C(=O)— |
| Br | Cl | CH₃ | —(CH₂)₂C(=O)— |
| H | Br | CF₃ | —(CH₂)₂C(=O)— |
| OCH₃ | CH₃ | OCH₃ | —CH=CHC(=O)— |
| CH₃ | CN | OC₂H₅ | —CH=CH—O— |
| NO₂ | F | H | —CH=CH—O— |
| H | CN | H | —C(CH₃)=C(CH₃)—O |
| SC₂H₅ | CN | H | —CH=CH—S— |
| H | H | Cl | S—CH=CH(CH₃)— |
| H | H | Cl | —CH=CH—CO— |
| F | F | H | —S—(CH₂)₂O— |
| Cl | Cl | H | —CH₂SC(CH₃)₂O— |

The benzoyl thioureas of formula I are most easily prepared through the reaction of a bicycloxyaniline II with a benzoylisothiocyanate III according to the reaction scheme A. As also illustrated, III is prepared through the reaction of a benzoyl chloride with potassium thiocyanate.

Scheme A

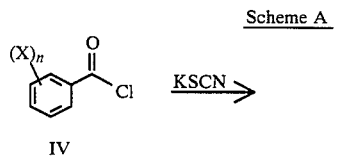

-continued
Scheme A

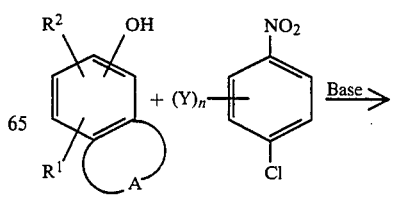

wherein: X, Y, R¹, R², A, n and M are as previously described.

The reaction of potassium thiocyanate with IV occurs smoothly with the aid of a phase transfer catalyst in an organic solvent. Suitable catalysts include the cyclic polyether phase transfer catalysts as well as tetralkylammonium salts. Suitable solvents can include toluene and acetonitrile. This reaction progresses smoothly within a temperature range of from ambient conditions to the reflux point of the solvent.

While many of the benzoyl isothiocyanates III are stable substances and can be isolated it is preferred that no isolation be done. Rather, the bicyclooxyaniline II is added directly to the reaction mixture containing III. The reaction temperature is maintained at a temperature between ambient and 50° C. during this addition. An inert organic solvent may be employed during this addition and is usually the same as used for the preparation of III. However, any inert organic solvent would serve.

The intermediates shown in Scheme A can be readily prepared according to well known procedures in the chemical literatures.

The bicyclooxyanilines II can be prepared according to the two step sequence illustrated below:

-continued $$O_2N-\underset{(Y)_m}{\bigcirc}-O-\underset{R^1}{\overset{R^2}{\bigcirc}}\underset{A}{\bigcirc} \xrightarrow{\text{Reduction}}$$

$$H_2N-\underset{(Y)_m}{\bigcirc}-O-\underset{R^1}{\overset{R^2}{\bigcirc}}\underset{A}{\bigcirc}$$
II wherein: Y, $R^1$, $R^2$, n, m and A are as previously defined.

The reaction of the bicyclic phenol with a 4-chloro-1-nitrobenzene proceeds in the presence of a base in an inert solvent at an elevated temperature to afford the nitro-ether.

Suitable bases include sodium hydride, potassium hydroxide and potassium carbonate. Suitable solvents include methyl ethyl ketone, dimethylformamide and dimethylsulfoxide. If the reaction is heterogeneous a phase-transfer agent such as quaternary ammonium halide or crown ether complex may be added.

The reaction of the nitro ether to the aniline II can be accomplished under a hydrogen atmosphere using a heterogeneous hydrogenation catalyst. Such catalysts include platinum or palladium on an inert support or a Raney nickel catalyst. In general these reductions can be performed under a wide range of temperatures and pressures. However, it is preferable to use a pressure range 80–120 psi at ambient temperature. The solvents of choice include aromatic hydrocarbons, such as toluene or alcohols such as ethanol. Alternatively, this reduction may also be accomplished by a chemical reductant such as a transition metal or its salts in a mineral acid solution. In general tin or iron and their salts in hydrochloric acid are preferred. A co-solvent such as dioxane or alcohols may be added to improve the reactant solubility in the reaction medium. The aniline II can be converted to the isocyanate VI by the reaction with phosgene employing generally accepted procedures.

Both the bicyclicphenols and the nitrochlorobenzenes are available commercially or may be prepared by well known methods from the chemical literature.

The compounds contemplated in this invention may be applied as insecticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultraviolet light, oxidation, or hydrolysis in the presence of moisture or, at least, such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are now compatible with substantially any other constituents of the spray schedule, and they may be used in the soil, upon the seeds, or the roots of plants without injuring either the seeds or roots of plants.

Mixtures of the active compounds may be employed if desired as well as combinations of the active compounds of this invention with other biologically active compounds or synergists.

The following examples illustrate the best mode presently contemplated for the practice of this invention:

EXAMPLE 1

Preparation of
1-(4-[4-Chloro-1-naphthoxy]-3,5-dichlorophenyl)-3-(2,6-difluorobenzoyl)thiourea Part A: Preparation of
4-(4-chloro-1-naphthoxy)-3,5-dichloro-1-nitrobenzene To a mixture containing 28.02 g (0.203 mole) of anhydrous potassium carbonate and 30.26 g (0.134 mole) of 3,4,5-trichloro-1-nitrobenzene in 300 ml dry DMF under an atmosphere of nitrogen and at room temperature was added 30.04 g (0.168 mole) of 4-chloro-1-naphthol. The flask was then placed in an oil bath which was heated.

An internal reaction temperature of 105° C. was reached and maintained for 20 hours. After cooling the reaction mixture to room temperature most of the DMF was removed under vacuum. The residue was taken up in 1.5L of 1:1 EtOAc to Et₂O and 300 ml of H₂O. The layers were separated and washed twice with 5% NaOH, twice with H₂O, and finally once with a saturated aqueous NaCl solution. After drying over anhydrous Na₂SO₄ removal of the solvents afforded 48.73 g of a dark brown solid. This was recrystallized twice from hexane-ethyl acetate to afford 15.48 g of pale yellow needles; mp 121.5–123 C. NMR(CDCl₃): 6.18 (d, J=8 Hz, 1H), 7.25 (d, J-8 Hz, 1H) 8.4–8.7 (m, 2H), 8.0–8.5 (m, 4H, contains 8.25 [s]).

Part B: Catalytic Reduction of 4-(4-chloro-1-naphthoxy)-3,5-dichloro-1-nitrobenzene A 0.5 L rocking hydrogenerator was charged with a solution of 15.84 g of 4-(4-chloro-1-naphthoxy)-3,5-dichloro-1-nitrobenzene in 250 ml of toluene. To this was added 0.5 g at 5% Pt on carbon and the bomb sealed. Hydrogen was introduced to a pressure of 100 psi. The pressure of hydrogen was maintained between 80 and 100 psi until the hydrogen up-take ceased. The material was removed from the bomb and filtered through celite. Removal of the solvents from the filtrates afforded 13.99 g of white solid, m.p. 145°–147° C. NMR (DMSO-d₆): 5.72 (broad s, 2H), 6.38 (d,J=8 Hz, 1H), 6.82 (s, 2H), 7.3–8.7 (m, 5H).

Part C: Chemical Reduction of 4-(4-chloro-1-naphthoxy)-3,5-dichloro-1-nitrobenzene 37.47 g (0.1 moles) of 3,5-dichloro-4-(4-chloro-1-naphthoxy)-1-nitrobenzene were added carefully to an 80° C. solution of 75.6 g (0.335 moles) of stannous chloride, 67 ml of HCl, and 50 ml of dioxane. (Mechanical stirrer needed because of resulting thick suspension). The suspension was stirred an additional 30 minutes at reflux. The reaction was cooled and then poured into a beaker containing 134 g (3.3 moles) of NaOH in 340 ml of H₂O with an equal amount of ice. A white solid was filtered off, taken up in CHCl₃ and dried. Removal of the solvents afforded 32.21 g of a white solid.

Part D: Preparation of 1-(4-[4-Chloro-1-naphthoxy]-3,5-dichlorophenyl)-3-(2,6-difluorobenzoyl)thiourea To a mixture of 1.4 g of potassium thiocyanate and 1.0 mg of 18-Crown-6 in 15 ml CH₃CN which was cooled to 0° C. and placed under an atmosphere of nitrogen was slowly added a solution of 23 g of 2,6-diflurobenzoyl chloride in 15 ml of CH₃CN. The reaction mixture was stirred for 0.5 hr at 0° C. and then allowed to warm to room temperature. After 0.5 hr at an IR spectrum of an aliquot indicated complete disappearance of the acid chloride. To the reaction mixture was then added 4.0 g of 4-(4-chloro-1-naphthoxy)-3,5-dichloroaniline as a powder. After 0.5 hr at ambient temperature the reaction mixture was poured into 125 ml of cold water. A buff colored solid precipitated and was filtered. The filter cake was then washed with 120 ml of a 5:1 H₂O:CH₃CN solution. The crystals were then dried overnight in a vacuum oven at 50° C. This afforded 5.6 g of the desired thiourea as a pale yellow crystalline powder. mp 193°–195° C. NMR (D₆-DMSO): 6.43 (d, J-10 Hz, 1H), 7.0–817 (m, 10H contains singlet at 8.13), 12.35 (s, 1H), 12.62 (s, 1H).

EXAMPLE 2

Preparation of 1-(5-Chloro-4-[4-chloro-5,6,7,8-tetrahydro-1-naphthoxy]-2-methylphenyl)-3-(2-chlorobenzoyl)thiourea

Part A: Preparation of 4-Chloro-5-(4-chloro-5,6,7,8-tetrahydro-1-naphthoxy)-2-nitrotoluene To a solution containing 39.96 g of 4,5-dichloro-2-nitrotoluene and 39.30 g of 4-chloro-5,6,7,8-tetrahydro-1-naphthol in 250 ml of DMF under an atmosphere of nitrogen and at room temperature was added 3.87 g of anhydrous potassium carbonate. The resulting mixture was then heated to 110° C. After 20 hrs at 110° C., the reaction mixture was cooled to room temperature. The DMF was removed in vacuo. The residue was dissolved in 500 ml of warm toluene and filtered through celite. The filter cake was thoroughly washed with toluene. The solvents from the combined filtrates were removed to afford 67.04 g of tan powder. This material was recrystallized from a hexane-ethyl acetate mixture to afford 49.46 g of the desired product as light tan crystals. mp 139°–140° C. NMR (CDCl₃): 1.6–1.9 (m, 4H), 2.4–2.9 (m, 7H, contains singlet at 2.45), 6.51 (s, 1H), 6.73 (d, J-8 Hz, 1H), 7.18 (d, J=8 Hz, 1H), 8.15 (s, 1H).

Part B: Preparation of 5-Chloro-4-(4-chloro-5,6,7,8-tetrahydro-1-naphthoxy)-2-methylaniline To a solution of 45.0 g of 4-chloro-5-(4-chloro-5,6,7,8-tetrahydro-1-naphthoxy)-2-nitrotoluene in 1200 ml of toluene was added 4.5 g of 5% platinum on carbon catalyst. This mixture was then changed to a 2 L stirred Parr pressure reactor. The reactor was flushed twice with nitrogen, then twice with hydrogen and then finally filled with hydrogen to a pressure of 250 psig. The internal pressure was maintained between 200 psig and 250 psig while the internal temperature was maintained between 40° and 45° C. during the course of the reaction. When hydrogen uptake ceased, the reaction mixture was removed from the reactor and filtered through celite. Removal of the toluene in vacuo afforded a yellow oil which slowly solidified. Recrystallization from a hexane-ethyl acetate mixture afforded 39.14 g of the desired aniline as white crystals. mp=180° C. NMR (CDCl₃): 1.6–1.9 (m, 4H), 2.05 (s, 3H), 2.5–2.7 (m, 4H), 3.47 (broad s, 2H), 6.33 (d, J=8 Hz, 1H), 6.63 (s, 2H), 7.03 (d, J=8 Hz, 1H).

Part C: Preparation of 1-(5-Chloro-4-[4-chloro-5,6,7,8-tetrahydro-1-naphthoxy]-2-methylphenyl)-3-(2-chlorobenzoyl)thiourea A solution of 1.0 mg of 18-crown-6 in 15 ml of CH₃CN was placed under an atmosphere of nitrogen and cooled to 5° C. (internal). To this was slowly added via an addition funnel a solution of 0.94 g of 2-chlorobenzoyl chloride in 15 ml of CH₃CN. The resulting reaction mixture was stirred for 20 min. at 5° C. then warmed to room temperature. After 20 min. at room temperature a solution containing 1.55 g of 5-chloro-4-(4-chloro-5,6,7,8-tetrahydro-1-naphthoxy)-2-methylaniline in 5 ml of CH₃CN was added. After 0.5 hr. at ambient temperature the reaction mixture was poured into 100 ml of cold H₂O. The resulting mixture was filtered and the filtercake washed with 5:1 H₂O:CH₃CN. The filtercake was then dried overnight in a vacuum oven at 50° C. This afforded 2.40 g of the desired thiourea as a yellow, fluffy powder. mp 163°–166° C. NMR (d₆-DMSO): 1.5–1.9 (m, 4H), 2.25 (s, 3H), 2.6–3.0 (m, 4H), 6.60 (d, J=9 Hz, 1H), 6.70 (s, 1H), 7.20 (d, J=9 Hz, 1H), 7.3–8.1 (m, 5H), 12.25 (broad s, 2H).

EXAMPLE 3

Preparation of 1-(3,5-Dichloro-4-[2,3-dihydro-2,2-dimethyl-7-benzofuranyloxy]phenyl)-3-(2,6-diflurobenzoyl)Thiourea Part A: Preparation of 3,5-Dichloro-4-(2,3-dihydro-2,2-dimethyl-7-benzofuranyloxy)-1-nitrobenzene To a solution containing 32.83 g of 1,2,3-trichloro-5-nitrobenzene and 26.11 g of 2,3-dihydro-2,2-dimethyl-7-hydroxybenzofuran in 300 ml of methyl ethyl ketone under an atmosphere of nitrogen and at room temperature was added 21.98 g of anhydrous potassium carbonate. The reaction mixture was heated to reflux. Reflux was maintained for 30 hrs. The reaction mixture was cooled to room temperature and the solvents removed. The tan solid residue was dissolved in hot hexane containing a little ethyl acetate. This was filtered and the filtrate allowed to cool to room temperature then placed in freezer to cool further to promote crystallization. The crystals were collected and placed in a vacuum dessicator for drying. A second crop of crystals was obtained from the mother liquors. This afforded 29.2 g of pale tan crystals. mp 105°–110° C. NMR (CDCl₃): 1.47 (s, 6H), 3.03 (s, 2H), 6.3–7.0 (m, 3H), 8.22 (s, 2H).

Part B: Preparation of 3,5-Dichloro-4-(2,3-dihydro-2,2-dimethyl-7-benzofuranyloxy)aniline To a solution of 29.2 g of 3,5-dichloro-4-(2,3-dihydro-2,2-dimethyl-7-benzofuranyloxy)-1-nitrobenzene in 500 ml of toluene was added 2.3 g of 5% platinum on carbon catalyst. This mixture was then charged into a 1 L rocking Parr reactor. The reactor was purged twice with nitrogen then twice with hydrogen, then finally filled with hydrogen to a pressure of 100 psig. The hydrogen pressure was maintained between 75 and 100 psig during the course of the reaction. After hydrogen uptake ceased, the reaction mixture was removed from the reactor. This was filtered through celite. Removal of the solvents afforded 23.95 g of off-white crystals. mp 140°–145° C. NMR (CDCl₃): 1.53 (s, 6H), 3.03 (s, 2H), 3.70 (broad s, 2H), 6.2–7.0 (M, 5H, contains singlet at 6.62).

Part C: Preparation of 1-(3,5-Dichloro-4-[2,3-dihydro-2,2-dimethyl-7-benzofuranyloxy]phenyl)-3-(2,6-diflurobenzoyl)thiourea A solution of 1.0 mg of 18-Crown-6 in 25 ml of CH₃CN was placed under an atmosphere of nitrogen then cooled in an ice bath to 5° C. (internal). To this was then added a solution of 1.86 g of 2,6-diflurobenzoyl chloride in 25 ml of CH₃CN. The resulting mixture was stirred at 5° C. for 0.5 hr then allowed to warm to room temperature. After 0.5 hr at room temperature, 3.0 g of 3,5-dichloro-4-(2,3-dihydro-2,2-dimethyl-7-benzofuranyloxy)aniline was added as a powder. After 0.5 hr at room temperature this was poured into 125 ml of cold water. At this point an oil separated. This mixture was then extracted 2 times with 100 ml portions of CH₂Cl₂. The combined extracts were then dried over anhydrous sodium sulfate. After filtration removal of the solvents from the filtrates afforded 5.9 of an orange poweder. Recrystallization from a hexane-ethyl acetate mixture afforded 2.0 g of the desired product as an off white powder. mp 153°–154° C.

In a manner similar to that employed in Part A of Example 1, other bicyclyl nitrophenyl ethers were prepared. The structural formulas and melting points are set forth in Table A to D below:

TABLE A

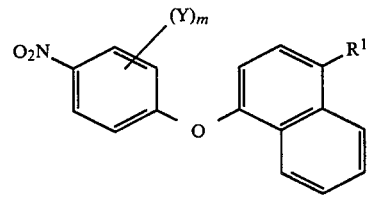

| (Y)ₘ | R¹ | m.p. (°C.) |
|---|---|---|
| H | H | 140° |
| H | Cl | 78–82° |
| 3-Cl | H | 79–81° |
| 3-Cl | Cl | 156–157° |
| 3-Cl | 2,4-Cl₂ | 131–132° |
| 3-Cl | OCH₃ | 124–128° |
| 3-Cl | N(CH₃)₂ | 92–94° |
| 3-CH₃ | H | oil |
| 3-CH₃ | Cl | 97–98° |
| 3-CH₃ | OCH₃ | 154–157° |
| 3-CF₃ | H | oil |
| 3-CF₃ | Cl | 77–78.5° |
| 3-OCH₃ | Cl | 94–95° |
| 3-OCH₃ | OCH₃ | 110–121° |
| 3,5-Br₂ | Cl | 163–164° |
| 3,5-Cl | H | 100–101° |
| 3,5-Cl | OCH₃ | 131–132° |
| 3,5-Cl | 2,4-Cl₃ | 128–130° |
| 3,-CH₃, 5-Cl | Cl | 135–137° |
| 3-CH₃, 5-Cl | OCH₃ | — |
| 2-CH₃, 5-Cl | Cl | 127–128° |
| 3,5-(CH₃)₂ | Cl | 145–146° |
| 2,5-(CH₃)₂ | Cl | 85–87° |
| 2,5-(CH₃)₂, 3-Cl | Cl | 135–137° |

TABLE B

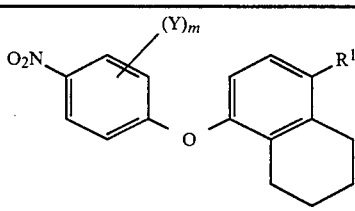

| (Y)$_m$ | R$^1$ | m.p. (°C.) |
|---|---|---|
| 3-Cl | H | 75–78° |
| 3-Cl | Cl | 92–96° |
| 3-CH | Cl | 117–120° |
| 3-CH | N(CH$_3$)$_2$ | — |
| 3-OCH$_3$ | Cl | 92–93° |
| 3-OCH$_3$ | N(CH$_3$)$_2$ | 110–113° |
| 3,5-Cl$_2$ | Cl | 178–180° |
| 3,5-Cl$_2$ | H | 138–141° |
| 3,5-Cl$_2$ | Cl | 151–154° |
| 3,5-Cl$_2$ | N(CH$_3$)$_2$ | — |
| 3-CH$_3$—5-Cl | Cl | 157–159° |
| 2-CH$_3$—5-Cl | Cl | 139–140° |
| 3,5-(CH$_3$)$_2$ | Cl | 178–180° |
| 3,5-(CH$_3$)$_2$ | N(CH$_3$)$_2$ | 121–122° |
| 2,5-(CH$_3$)$_2$ | Cl | 124–125.5° |
| 2,5-(CH$_3$)$_2$, 3-Cl | Cl | 157–158° |
| 2,5-(CH$_3$)$_2$, 3-Cl | N(CH$_3$)$_2$ | 110–112° |

TABLE C

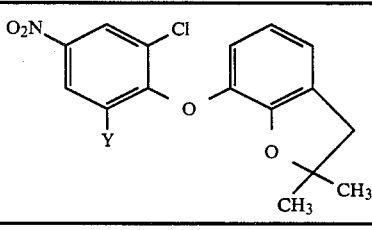

| (Y)$_m$ | R$^1$ | R$^3$ | m.p. (°C.) |
|---|---|---|---|
| H | H | H | 81–82° |
| 3-Cl | H | Br | 128–131° |
| 3-Cl | Br | Br | 152–154° |
| 3-CH$_3$ | Br | Br | 143–144° |
| 3,5-Cl$_2$ | H | H | 118.5–119° |
| 3,5-Cl$_2$ | H | Br | 181–183° |

TABLE D

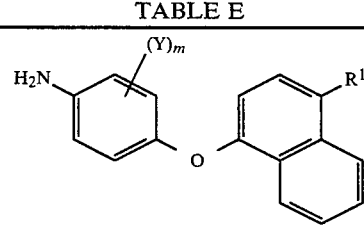

| | m.p. (°C.) |
|---|---|
| Y=H | 132–133° |
| Y—Cl | 105–110° |

In a manner similar to that employed in Part B of Example 1, other bicyclo-oxyanilines were prepared. The structural formulas and melting points are set forth in Tables E to I below:

TABLE E

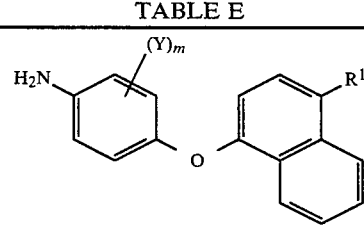

| (Y)$_m$ | R$^1$ | m.p. (°C.) |
|---|---|---|
| 3-Cl | H | oil |
| 3-Cl | Cl | 95–96° |
| 3-Cl | 2,4-Cl$_2$ | — |
| 3-Cl | OCH$_3$ | 100–102° |
| 3-CH$_3$ | H | 100–102° |
| 3-CH$_3$ | OCH$_3$ | 100–102° |
| 3-CF$_3$ | H | oil |
| 3-CF$_3$ | Cl | 75° |
| 3-OCH$_3$ | OCH$_3$ | 98–101° |
| 3,5-Cl$_2$ | H | 108–109° |
| 3,5-Cl$_2$ | OCH$_3$ | 168–169° |
| 3,5-Cl$_2$ | 2,4-Cl$_2$ | — |
| 3-CH$_3$, 5-Cl | Cl | 111–113° |
| 3-CH$_3$, 5-Cl | OCH$_3$ | 126–128° |
| 2,5-(CH$_3$)$_2$ | Cl | 84–88° |
| 2,5-(CH$_3$)$_2$, 3-Cl | Cl | 123–125° |

TABLE F

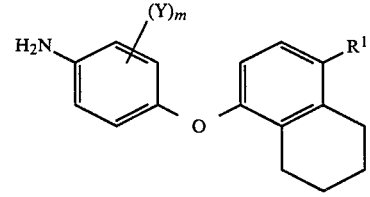

| (Y)$_m$ | R$^1$ | m.p. (°C.) |
|---|---|---|
| 3-Cl | H | 62–63° |
| 3-Cl | Cl | 70–73° |
| 3-CH$_3$ | Cl | 82–83° |
| 3-CH$_3$ | N(CH$_3$)$_2$ | oil |
| 3-OCH$_3$ | Cl | 105–107° |
| 3-OCH$_3$ | N(CH$_3$)$_2$ | 120–125° |

TABLE F-continued

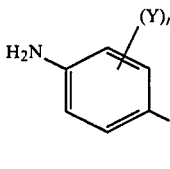

| (Y)$_m$ | R$^1$ | m.p. (°C.) |
|---|---|---|
| 3,5-Cl | Cl | — |
| 3,5-Cl | N(CH$_3$)$_2$ | 117–120° |
| 3-CH$_3$, 5-Cl | Cl | 161–162° |
| 2-CH$_3$, 5-Cl | Cl | 108° |
| 3,5-(CH$_3$)$_2$ | Cl | 134–135° |
| 3,5-(CH$_3$)$_2$ | N(CH$_3$)$_2$ | 102–105° |
| 2,5-(CH$_3$)$_2$, 3-Cl | N(CH$_3$)$_2$ | 124–126° |

TABLE G

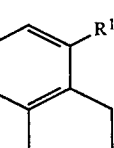

| (Y)$_m$ | R$^1$ | R$^2$ | m.p. (°C.) |
|---|---|---|---|
| 3-Cl | H | H | 82–83° |
| 3-Cl | H | Br | 112–113° |
| 3-Cl | Br | Br | 121–123° |
| 3-CH$_3$ | Br | Br | 145–150° |
| 3,5-Cl$_2$ | H | H | 100–102° |
| 3,5-Cl$_2$ | H | Br | 164–166° |

TABLE H

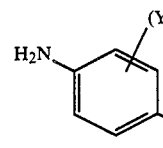

| Y = H | 102–104° |
|---|---|
| Y = Cl | 142–145° |

TABLE I

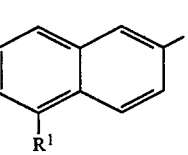

112–114°

In a manner similar to that employed in Part C of Example 1, the bicycloxy-anilines set forth in Tables J and K were prepared following the chemical reduction technique.

TABLE J

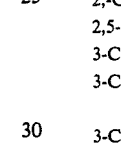

| (Y)$_m$ | R$^1$ | m.p. (°C.) |
|---|---|---|
| H | H | oil |
| H | Cl | oil |
| 3-Cl | N(CH$_3$)$_2$ | oil |
| 3-CH$_3$ | Cl | 75° |
| 3-OCH$_3$ | Cl | — |
| 3,5-Br$_2$ | Cl | 168–171° |
| 3,5-Cl$_2$ | 2,4-Cl$_2$ | |
| 2,-CH$_3$, 5-Cl | Cl | 90–92° |
| 2,5-(CH$_3$)$_2$ | Cl | 96–98° |
| 3-Cl | SO$_3$Na | — |
| 3-Cl | SO$_2$N(CH$_3$)$_2$ | — |
| 3-Cl | 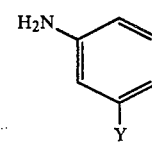 | — |
| 3-Cl | 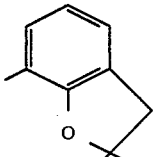 | — |

TABLE K

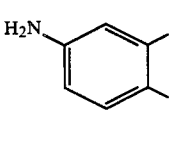

| (Y)$_m$ | R$^1$ | m.p. (°C.) |
|---|---|---|
| 3,5-Br$_2$ | Cl | 108–111° |
| 3,5-Cl$_2$ | H | 106–112° |
| 3,5-Cl$_2$ | Cl | — |
| 2,5-(CH$_3$)$_2$ | Cl | — |
| 2,5-(CH$_3$)$_2$ | Cl | 111–116° |

EXAMPLES 1–42

In a manner similar to that employed in the preceding examples, and using one of the synthesis schemes previously disclosed, other urea compounds were prepared. The identity of the substituents on the generic formula and the analytical data are set forth in Tables 9–12 below:

TABLE 9
Physical Properties of 1-(4-[1-Naphthoxy]phenyl)-3-benzoyl Thioureas

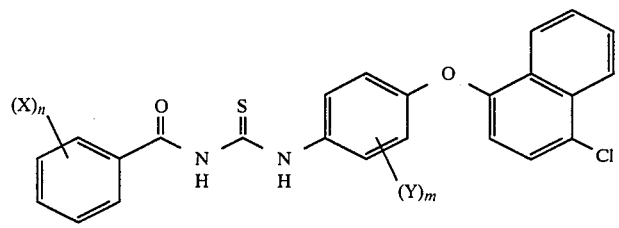

| Example | $(X)_n$ | $(Y)_m$ | mp (°C.) | Molecular Formula | Calc C | Calc H | Calc N | Found C | Found H | Found N |
|---|---|---|---|---|---|---|---|---|---|---|
| 1 | 2,6-$F_2$ | 3,5-$Cl_2$ | 193–195 | $C_{24}H_{13}Cl_3F_2N_2O_2S$ | 53.60 | 2.44 | 5.21 | 53.96 | 2.50 | 5.08 |
| 4 | 2-Cl | 3,5-$Cl_2$ | 185–187 | $C_{24}H_{14}Cl_4N_2O_2S$ | 53.75 | 2.64 | 5.23 | 53.47 | 2.76 | 5.30 |
| 5 | 2-F | 3,5-$Cl_2$ | 169–170 | $C_{24}H_{14}Cl_3FN_2O_2S$ | 55.45 | 2.72 | 5.39 | 55.96 | 2.78 | 5.41 |
| 6 | 4-Cl | 3,5-$Cl_2$ | 207–209 | $C_{24}H_{14}Cl_4N_2O_2S$ | 53.75 | 2.64 | 5.23 | 53.90 | 2.71 | 5.25 |
| 7 | H | 3,5-$Cl_2$ | 204–205 | $C_{24}H_{15}Cl_3N_2O_2S$ | 57.44 | 3.02 | 5.58 | 57.65 | 3.38 | 5.53 |
| 8 | 2,6-$F_2$ | 3-Cl | 204–205.5 | $C_{24}H_{14}Cl_2F_2N_2O_2S$ | 57.27 | 2.81 | 5.57 | 56.68 | 2.86 | 5.49 |
| 9 | 2-Cl | 3-Cl | 187–188 | $C_{24}H_{15}Cl_3N_2O_2S$ | 57.44 | 3.02 | 5.58 | 57.36 | 3.20 | 5.55 |
| 10 | 4-Cl | 3-Cl | 156–159 | $C_{24}H_{15}Cl_3N_2O_2S$ | 57.44 | 3.02 | 5.58 | 57.32 | 3.22 | 5.40 |
| 11 | 2,6-$F_2$ | 3-$CH_3$ | 182–183.5 | $C_{25}H_{17}ClF_2N_2O_2S$ | 62.18 | 3.56 | 5.80 | 61.18 | 3.73 | 5.79 |
| 12 | 2-Cl | 3-$CH_3$ | 175–177 | $C_{25}H_{18}Cl_2N_2O_2S$ | 62.37 | 3.78 | 5.82 | 62.72 | 3.85 | 5.94 |
| 13 | 4-Cl | 3-$CH_3$ | 164–166 | $C_{25}H_{18}Cl_2N_2O_2S$ | 62.37 | 3.78 | 5.82 | 62.24 | 4.04 | 5.82 |
| 14 | H | 3-$CH_3$ | 161–162 | $C_{25}H_{19}ClN_2O_2S$ | 67.17 | 4.29 | 6.27 | 66.79 | 4.56 | 6.32 |
| 15 | 2-F | 3-$CH_3$ | 119–121 | $C_{25}H_{18}ClFN_2O_2S$ | 64.58 | 3.91 | 6.03 | 64.64 | 3.92 | 6.00 |
| 16 | 2-Cl | 3,5-$(CH_3)_2$ | 199–200 | $C_{26}H_{20}Cl_2N_2O_2S$ | 63.03 | 4.08 | 5.66 | 63.19 | 4.07 | 5.72 |
| 17 | 2,6-$F_2$ | 2-$CH_3$—5-Cl | 163.5–165 | $C_{25}H_{16}Cl_2F_2N_2O_2S$ | 58.03 | 3.12 | 5.42 | 57.86 | 3.20 | 5.45 |
| 18 | 2-Cl | 2-$CH_3$—5-Cl | 167–168 | $C_{25}H_{17}Cl_3N_2O_2S$ | 58.20 | 3.33 | 5.43 | 58.01 | 3.34 | 5.36 |
| 19 | 4-Cl | 2-$CH_3$—5-Cl | 188–189 | $C_{25}H_{17}Cl_3N_2O_2S$ | 58.20 | 3.33 | 5.43 | 57.81 | 3.30 | 5.34 |
| 20 | H | 2-$CH_3$—5-Cl | 188–189 | $C_{25}H_{18}Cl_2N_2O_2S$ | 62.37 | 3.78 | 5.82 | 62.66 | 3.89 | 5.77 |
| 21 | 2,6-$F_2$ | 2,5-$(CH_3)_2$—3-Cl | 199–201 | $C_{26}H_{18}Cl_2F_2N_2O_2S$ | 58.76 | 3.42 | 5.27 | 60.03 | 3.54 | 5.13 |
| 22 | 2-Cl—6-F | 2,5-$(CH_3)_2$—3-Cl | 219–220 | $C_{26}H_{18}Cl_3FN_2O_2S$ | 56.99 | 3.32 | 5.11 | 67.03 | 3.28 | 5.05 |
| 23 | 2-Cl | 2,5-$(CH_3)_2$—3-Cl | 178.5–181.5 | $C_{26}H_{19}Cl_3N_2O_2S$ | 58.93 | 3.62 | 5.29 | 60.00 | 3.70 | 5.25 |
| 24 | 4-Cl | 2,5-$(CH_3)_2$—3-Cl | 211.5–212.5 | $C_{26}H_{19}Cl_3N_2O_2S$ | 58.93 | 3.62 | 5.29 | 58.80 | 3.72 | 5.23 |
| 25 | H | 2,5-$(CH_3)_2$—3-Cl | 179–180 | $C_{26}H_{20}Cl_2N_2O_2S$ | 63.03 | 4.08 | 5.66 | 62.79 | 4.06 | 5.72 |

TABLE 10
Physical Properties of 1-(4-[5,6,7,8-Tetrahydro-1-naphthoxy]phenyl)-3-benzoyl Thioureas

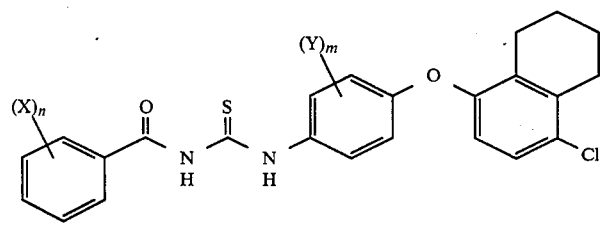

| Example | $(X)_n$ | $(Y)_m$ | mp(°C.) | Molecular Formula | Calc C | Calc H | Calc N | Found C | Found H | Found N |
|---|---|---|---|---|---|---|---|---|---|---|
| 2 | 2-Cl | 2-$CH_3$—5-Cl | 153.5–156.5 | $C_{25}H_{21}Cl_3N_2O_2S$ | 57.75 | 4.10 | 5.39 | 57.47 | 4.16 | 5.33 |
| 26 | 2,6-$F_2$ | 2-$CH_3$—5-Cl | 164–166 | $C_{25}H_{20}Cl_2F_2N_2O_2S$ | 57.58 | 3.87 | 5.37 | 57.78 | 4.00 | 5.70 |
| 27 | 4-Cl | 2-$CH_3$—5-Cl | 200.5–201 | $C_{25}H_{21}Cl_3N_2O_2S$ | 57.75 | 4.60 | 5.39 | 58.54 | 4.33 | 5.48 |
| 28 | H | 2-$CH_3$—5-Cl | 187–188.5 | $C_{25}H_{22}Cl_2N_2O_2S$ | 61.86 | 4.58 | 5.77 | 61.78 | 4.69 | 5.78 |
| 29 | 2,6-$F_2$ | 3,5-$Cl_2$ | 193–194 | $C_{24}H_{17}Cl_3F_2N_2O_2S$ | 53.19 | 3.17 | 5.17 | 53.23 | 3.18 | 5.15 |
| 30 | 2-F | 3,5-$Cl_2$ | 194–195.5 | $C_{24}H_{18}Cl_3FN_2O_2S$ | 55.02 | 3.47 | 5.35 | 54.60 | 3.67 | 5.18 |
| 31 | 2-Cl | 3,5-$Cl_2$ | 175.5–177.5 | $C_{24}H_{18}Cl_4N_2O_2S$ | 53.35 | 3.36 | 5.19 | 53.47 | 3.43 | 5.13 |
| 32 | 4-Cl | 3-$CH_3$ | 161–162 | $C_{25}H_{22}Cl_2N_2O_2S$ | 61.80 | 4.57 | 5.77 | 62.06 | 4.75 | 5.61 |

TABLE 11
Physical Properties of 1-(4-[2-Naphthoxy]phenyl)-3-benzoyl Thioureas

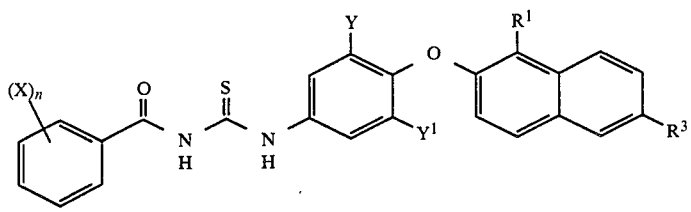

| Example | $(X)_1$ | Y | $Y^1$ | $R^1$ | $R^3$ | mp(°C.) | Molecular Formula | Calc C | Calc H | Calc N | Found C | Found H | Found N |
|---|---|---|---|---|---|---|---|---|---|---|---|---|---|
| 33 | 2,6-$F_2$ | Cl | H | Br | Br | 215–216 | $C_{24}H_{13}Br_2ClF_2N_2O_2S$ | 45.99 | 2.10 | 4.47 | 46.08 | 2.24 | 4.27 |
| 34 | 2,6-$F_2$ | $CH_3$ | H | Br | Br | 218–218.5 | $C_{26}H_{16}Br_2F_2N_2O_2S$ | 49.52 | 2.66 | 4.62 | 29.54 | 2.68 | 4.59 |
| 35 | 2-Cl | H | $CH_3$ | Br | Br | 210–210.5 | $C_{25}H_{17}Br_2ClN_2O_2S$ | 49.64 | 2.84 | 4.63 | 49.56 | 2.80 | 4.56 |
| 36 | 4-Cl | $CH_3$ | H | Br | Br | 192–193 | $C_{25}H_{17}Br_2ClN_2O_2S$ | 49.64 | 2.84 | 4.63 | 49.51 | 2.83 | 4.49 |
| 37 | 2,6-$F_2$ | Cl | Cl | H | Br | 193.5–194 | $C_{24}H_{13}Br_2Cl_2N_2O_2S$ | 49.50 | 2.25 | 4.81 | 49.54 | 2.00 | 4.90 |
| 38 | 2-Cl | Cl | Cl | H | Br | 173.5–174.5 | $C_{24}H_{14}BrCl_3N_2O_2S$ | 49.64 | 2.43 | 4.82 | 49.74 | 2.46 | 4.70 |
| 39 | 4-Cl | Cl | Cl | H | Br | 200.5–201.5 | $C_{24}H_{14}BrCl_3N_2O_2S$ | 49.64 | 2.43 | 4.82 | 49.46 | 2.47 | 4.72 |

TABLE 12
Physical Properties of 1-(Bicylcooxyaryl)-3-benzoyl Thioureas

| Example | Structure | Molecular Formula | Calc C | Calc H | Calc N | Found C | Found H | Found H |
|---|---|---|---|---|---|---|---|---|
| 3 | (structure) | $C_{24}H_{19}Cl_3N_2O_2S$ | 55.23 | 3.67 | 5.37 | 55.35 | 3.60 | 5.43 |
| 40 | (structure) | $C_{24}H_{18}Cl_2F_2N_2O_2S$ | 55.07 | 3.46 | 5.35 | 54.81 | 3.63 | 5.60 |
| 41 | (structure) | $C_{24}H_{16}ClF_2N_3O_2S$ | 59.56 | 3.33 | 8.68 | 59.84 | 3.34 | 8.69 |
| 42 | (structure) | $C_{24}H_{17}F_2N_3O_3S$ | 61.93 | 3.68 | 9.03 | 61.74 | 3.86 | 9.16 |

The novel compositions described by the preceding formulae are, with varying degrees of efficiency, useful in combatting insect and mite pests. The insecticidal activity of the compounds prepared according to this invention is summarized in Table 13. In addition, selected compounds have exhibited miticidal activity. This is shown in Table 14. Table 15 gives comparative data of several compounds of this invention with two prior art compounds.

Certain of the test compounds were prepared by dissolving 375 mg of compound in 7.5 ml of dimethylformamide. Fifteen ml of acetone containing 37.5 mg (10 percent of the weight of test compound) of an alkylphenoxy polyethoxyethanol surfactant, as a wetting-/emulsifying/dispersing agent was added to the dimethylformamide solution. Fifty-two and a half ml of water was mixed into the dimethylformamide-acetone mixture to give roughly 75 ml of a suspension containing the compound in solution or in finely divided form. The thus prepared stock suspension contained 0.5 percent by weight of compound. The test concentrations in parts per million by weight employed in the tests described hereinbelow were obtained by appropriate dilutions of the stock suspension with water. The test procedures were as follows:

Southern Armyworm Leaf Spray Bait Test

Second instar larvae (weighing about 2 mg) of the southern armyworm (Spodoptera eridania, (Cram.), reared on Tendergreen bean plants at a temperature of 80°±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 40 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°-85° F. for five days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Second instar larvae (weighing about 6 mg) of the Mexican bean beetle. (Epilachna varivestic, Muls.), reared on Tendergreen bean plants at a temperature of B 80°±5° F. and 50±5 percent relative humidity, were the test insects.

For certain of the tests second instar larvae (weighing about 6 mg) of the Mexican bean beetle (Epilachna varivestis, Muls), reared on Seiva Pole lima bean plants at a temperature of 80°±5° F. and 50±5 percent relative humidity, were the test insects.

The test compounds were formulated by diluting the stock suspenson with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 40 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F., for five days. Although the larvae could easily consume the leaf within 24 to 48 hours, no more food was added. Larvae which were unable to move the length of the body, even upon stimulation, were considered dead.

Mite Foilage Spray Test

Adults and nymphal stages of the two-spotted mite (*Tetranychus urticae* Koch) reared on Tendergreen beans under controlled conditions (80+5° F. and 50±5 percent relative humidity). Infested leaves from the stock culture are placed on the primary leaves of 2 bean plants 6-8 inches in height. A sufficient number of mites for testing (150-200) were transferred from the excised leaves to the fresh plants.

Infested Tendergreen bean plants of standard height and age are placed on a revolving turntable. A formulated water mixture of the chemical (100 mL) is applied to the plants by use of a DeVilbiss spray gun with air pressure set at 40 pounds. Application of this volume of formulated compound takes 25 seconds. This volume of spray is sufficient to wet the plants to run-off.

The test compounds are formulated by a standard procedure of solution in acetone/DMF, addition of an emulsifier, and dilution with water. Primary spray applications are conducted at 500 ppm.

The treated plants are held at 80 ±5° F. and 50±5 percent relative humidity for a period of 7 days when mortality counts of motile forms (adults and nymphs) are made.

Microscopic examination of motile forms is made on one leaf from each of the 2 test plants. Any individual which is capable of locomotion upon stimulation is considered living.

MITE OVICIDE TEST

The eggs of the two-spotted mite (*Tetranuchus urticae* (Koch) are obtained from adults reared on Tendergreen beans under controlled conditions 80±5° F. and 50±5 percent relative humidity). Heavily infested leaves from the stock culture are placed on uninfested bean plants. Females are allowed to oviposit for a period of 24 hours, and the leaves of the plants are then dipped in a 1000 ppm solution of TEPP in order to kill the motile forms and prevent additional egg laying. TEPP does not affect the viability of the eggs.

The plants are placed on a revolving turntable. A formulated water mixture of the chemical (100 mL) is applied to the plants by use of a DeVilbiss spray gun with air pressure set at 40 pounds. Application of this volume of formulated compound takes 25 seconds. This volume of spray is sufficient to wet the plants to runoff.

An equivalent amount of a water solution containing acetone and emulsifier in the same concentrations as the insecticidal mixture but without the candidate insecticide is also sprayed on other infested plants as a check or control The test compounds are formulated by a standard procedure of solution in acetone, addition of an emulsifier, and dilution with water. Primary screening tests are conducted at 500 ppm.

The treated plants are held at 80±5° F. and 50±5 percent relative humidity for 7 days after which counts are made.

Microscopic examination is made of the plant leaves, and the number of unhatched eggs (considered dead) and empty egg shells (living eggs) are noted.

MITE LARVACIDAL TEST METHOD

The eggs of the two-spotted mite (*Tetranychus urticae* (Koch) are obtained from adults reared on Tendergreen beans under controlled conditions 80±5° F. and 50±5 percent relative humidity). Heavily infested leaves from the stock culture are placed on uninfested bean plants. Females are allowed to oviposit for a period of 24 hours, and the leaves of the plants are then dipped in a 1000 ppm solution of TEPP in order to kill the motile forms and prevent additional egg laying. TEPP does not affect the viability of the eggs. The TEPP treated mite infested plants are held at 80±5° F. and 50±5 percent relative humidity until the eggs hatch in 3–4 days. Then the larvae are transferred to bean plants 6–8 inches in height. A sufficient number of larvae for testing (50–100) were transferred from TEPP treated leaves to the fresh plants in 24 hours.

Infested Tendergreen bean plants are placed on a revolving turntable. Test compounds are formulated with DMF, acetone, and a 3 to 1 mixture of Triton 172 and 152, respectively and then diluted in water to appropriate concentrations of chemical for application to the infested plants by use of a DeVilbiss spray gun with air pressure set at 40 pounds. The volume of 100 ml. is sufficient to wet the plants to run off. A blank formulation is used for the control.

The treated plants are held at 80±5° F. and 50±5 percent relative humidity for a period of five to six days, when mortality counts of the larvae are made.

TABLE 13

Insecticidal Activity of 1-(4-Bicyclooxyphenyl)-3-benzoyl Thioureas

| Example | Mortality Rating[1] | |
|---|---|---|
|  | SAW[2] | MBB[3] |
| 1 | A | A |
| 2 | A | A |
| 3 |  |  |
| 4 | A | A |
| 5 | A | A |
| 6 | C | C |
| 7 | A |  |
| 8 | A | A |
| 9 | A | A |
| 10 | C | C |
| 11 | A | A |
| 12 | A | A |
| 13 | C | C |
| 14 | A | C |
| 15 | A | A |
| 16 | A | A |
| 17 | A | A |
| 18 | A | A |
| 19 | C | C |
| 20 | A | C |
| 21 | A | A |
| 22 | A | A |
| 23 | A | A |
| 24 | C | C |
| 25 | A | A |
| 26 | A | A |
| 27 | C | C |
| 28 | A | C |
| 29 | A | A |
| 30 | A | A |
| 31 | A | A |
| 32 | C | C |
| 33 | A | A |
| 34 | A | C |
| 35 | A | C |
| 36 | C | C |
| 37 | A | A |
| 38 | A | C |
| 39 | C | C |

[1]A = 71–100% control
B = 31–70% control
C = 0–30% control
[2]Southern armyworm
[3]Mexican bean beetle

TABLE 14

Miticidal Activity of 1-(4-Bicyclooxyphenyl)-3-benzoyl Thioureas

| Example | Mortality Rating Against Two-spotted Mite[1] | | |
|---|---|---|---|
|  | Adults | Larvae | Eggs |
| 1 | C | A | C |
| 4 | C | A | C |
| 8 | C | A | C |
| 9 | C | A | C |
| 12 | B | — | C |
| 25 | B | — | C |
| 26 | C | — | A |
| 31 | C | — | A |

[1]A = 71–100% kill
B = 31–70% kill
C = 0–30% kill

TABLE 15

Prior Art Thioureas vs. Naphthoxyphenyl Benzoyl

| | % Mortality | | |
|---|---|---|---|
| | Concentration (ppm) | SAW[(1)] | MBB[(2)] |
| | 8 | 30 | 60 |
| | 2 | 0 | 0 |

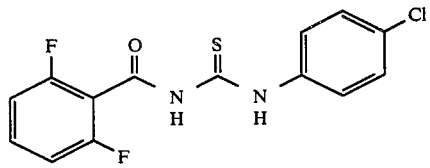

(Prior Art Cpd[3])

TABLE 15-continued

Prior Art Thioureas vs. Naphthoxyphenyl Benzoyl

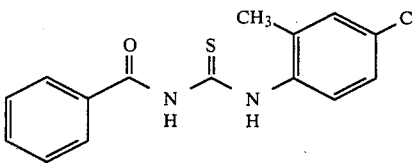

(Prior Art Cpd[4])

| | % Mortality | | |
|---|---|---|---|
| | Concentration (ppm) | SAW[1] | MBB[2] |
| | 125 | 100 | 0 |
| | 8 | 10 | — |
| 1 | 8 | 100 | 90 |
| | 2 | 100 | 90 |
| 2 | 16 | 100 | 100 |
| 8 | 8 | 100 | 100 |
| | 2 | 90 | 80 |
| 16 | 16 | 100 | 100 |
| | 4 | 90 | 100 |
| 17 | 16 | 100 | 100 |
| | 4 | 100 | 100 |
| 26 | 16 | 100 | 100 |
| | 4 | 60 | 100 |
| 29 | 8 | 100 | 100 |
| | 2 | 100 | 50 |
| 37 | 8 | 100 | 80 |
| | 2 | 100 | 10 |

[1]Southern armyworm
[2]Mexican bean beetle
[3]U.S. Pat. No. 3,989,842
[4]U.S. Pat. No. 4,160,037

Although the invention has been illustrated by the preceding examples, it is not to be construed as being limited to the materials employed therein; but rather, the invention relates to the generic area as hereinbefore disclosed. Various modifications and embodiments thereof can be made without departing from the spirit and scope thereof.

What is claimed is:

1. A compound having the formula

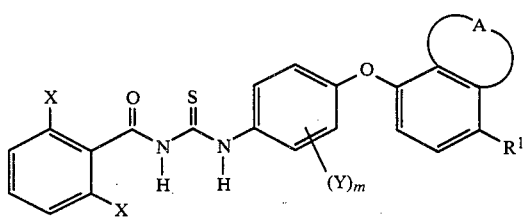

wherein:
X is individually hydrogen, halogen, or alkyl, polyhaloalkyl, alkoxy or polyhaloalkoxy having from one to three carbon atoms with the proviso that at least one X is other than hydrogen;
Y is individually halogen, or alkyl, polyhaloalkyl, alkoxy or polyhaloalkoxy having from one to six carbon atoms;
m is a value of from 2 to 4;
A is a tetramethylene or 1,3-butadienylene group; and
R[1] is halogen, amino, or alkyl, alkoxy, polyhaloalkyl, polyhaloalkoxy, mono- or di- alkylamino having up to six carbon atoms.

2. The compound of claim 1 having the formula

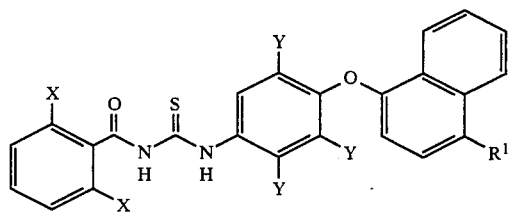

wherein:
X is individually hydrogen or halogen;
Y is individually halogen or alkyl having from one to six carbon atoms; and
R[1] is halogen, or alkoxy, mono- or di-alkylamino having up to six carbon atoms.

3. The compound of claim 2 wherein X is individually hydrogen, chloro or fluoro, Y is individually chloro or methyl, and R[1] is chloro, methoxy or mono- or di- methylamino.

4. The compound of claim 1 having the formula

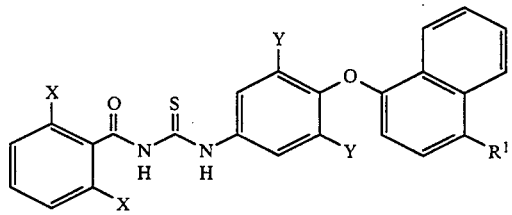

wherein:
X is individually hydrogen or halogen;
Y is individually halogen or alkyl having from one to six carbon atoms; and
R[1] is halogen, or alkoxy, mono- or di-alkylamino having up to six carbon atoms.

5. The compound of claim 4 wherein X is individually hydrogen, chloro or fluoro, Y is individually chloro or methyl, and R¹ is chloro, methoxy or mono- or di-methylamino.

6. The compound of claim 1 having the formula

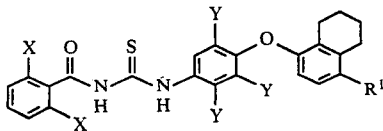

wherein:
X is individually hydrogen or halogen;
Y is individually halogen or alkyl having from one to six carbon atoms; and
R¹ is halogen, or alkoxy, mono- or di-alkylmino having up to six carbon atoms.

7. The compound of claim 6 wherein X is individually hydrogen, chloro or fluoro, Y is individually chloro or methyl, and R¹ is chloro, methoxy or mono- or di-methylamino.

8. The compound of claim 1 having the formula

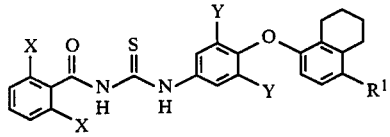

wherein
X is individually hydrogen or halogen;
Y is individually halogen or alkyl having from one to six carbon atoms; and
R¹ is halogen, or alkoxy, mono- or di-alkylamino having up to six carbon atoms.

9. The compound of claim 8 wherein X is individually hydrogen, chloro or fluoro, Y is individually chloro or methyl, and R¹ is chloro, methoxy or mono- or di-methylamino.

10. The compound of claim 1 having the formula

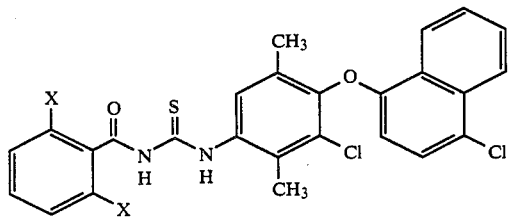

wherein:
X is individually hydrogen, chloro or fluoro.

11. The compound of claim 1 having the formula

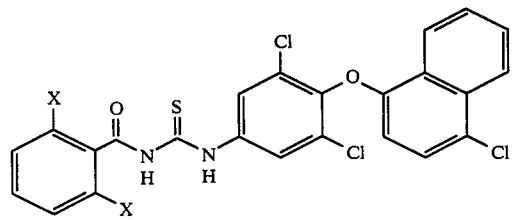

wherein:
X is individually hydrogen, chloro or fluoro.

12. The compound of claim 1 having the formula

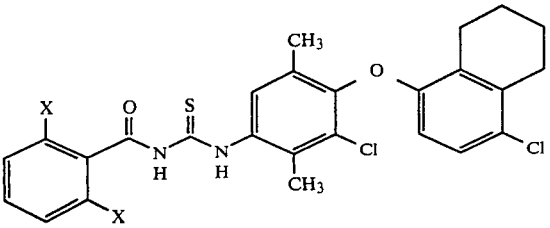

wherein:
X is individually hydrogen, chloro or fluoro.

13. The compound of claim 1 having the formula

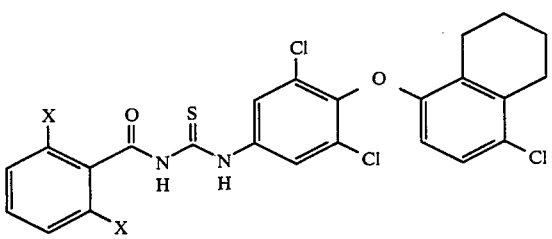

wherein:
X is individually hydrogen, chloro or fluoro.

14. The compound of claim 1 which is 1-(3-chloro-4-[4-chloro-1-naphthoxy[-2,5-dimethylphenyl)-3-(2-chlorobenzoyl)thiourea.

15. The compound of claim 1 which is 1-(3-chloro-4-[4-chloro-1-naphthoxy[-2,5-dimethylphenyl)-3-(2,6-difluorobenzoyl)thiourea.

16. The compound of claim 1 which is 1-(4-[4-chloro-1-naphthoxy]-3,5-dichlorophenyl)-3-(2-chlorobenzoyl)-thiourea.

17. The compound of claim 1 which is 1-(4-[4-chloro-1-naphthoxy]-3,5-dichlorophenyl)-3-(2,6-difluorobenzoyl)thiourea.

18. The compound of claim 1 which is 1-(3,5-dichloro-4-[4-chloro-5,6,7,8-tetrahydro-1-naphthoxy]-phenyl)-3-(2-chlorobenzoyl)thiourea.

19. The compound of claim 1 which is 1-(3,5-dichloro-4-[4-chloro-5,6,7,8-tetrahydro-1-naphthoxy]-phenyl)-3-(2,6-difluorobenzoyl)thiourea.

20. The compound of claim 1 which is 1-(3-chloro-4-[4-chloro-5,6,7,8-tetrahydro-1-naphthoxy]-5-methylphenyl)-3-(2,6-difluorobenzoyl)thiourea.

21. An insecticidal or acaricidal composition comprising an acceptable carrier and an insecticidally or acaricidally effective amount of the compound of claim 1.

22. An insecticidal or acaricidal composition comprising an acceptable carrier and an insecticidally or acaricidally effective amount of the compound of claim 2.

23. An insecticidal or acaricidal composition comprising an acceptable carrier and an insecticidally or acaricidally effective amount of the compound of claim 4.

24. An insecticidal or acaricidal composition comprising an acceptable carrier and an insecticidally or acaricidally effective amount of the compound of claim 6.

25. An insecticidal or acaricidal composition comprising an acceptable carrier and an insecticidally or acaricidally effective amount of the compound of claim 8.

26. An method of controlling insect and acarid pests which comprises subjecting said pests to an insecticidally or acaricidally effective amount of the composition of claim 21.

27. An method of controlling insect and acarid pests which comprises subjecting said pests to an insecticidally or acaricidally effective amount of the composition of claim 22.

28. An method of controlling insect and acarid pests which comprises subjecting said pests to an insecticidally or acaricidally effective amount of the composition of claim 23.

29. An method of controlling insect and acarid pests which comprises subjecting said pests to an insecticidally or acaricidally effective amount of the composition of claim 24.

30. An method of controlling insect and acarid pests which comprises sujecting said pests to an insecticidally or acaricidally effective amount of the composition of claim 25.

* * * * *